United States Patent [19]

Nguyen

[11] 4,305,393
[45] Dec. 15, 1981

[54] BRIGHT PEAT MOSS PRODUCT AND METHOD FOR MAKING SAME
[75] Inventor: Anh D. Nguyen, Brossard, Canada
[73] Assignee: Johnson & Johnson, New Brunswick, N.J.
[21] Appl. No.: 65,015
[22] Filed: Aug. 9, 1979
[51] Int. Cl.³ .............................................. A61F 13/16
[52] U.S. Cl. ..................................... 128/284; 128/285
[58] Field of Search ............... 128/270, 284, 287, 285, 128/290, 296

[56] References Cited
U.S. PATENT DOCUMENTS

| | | | |
|---|---|---|---|
| 639,864 | 12/1899 | Von Raitz | 128/270 |
| 3,889,678 | 6/1975 | Chatterjee et al. | 128/284 |
| 3,900,378 | 8/1975 | Yen et al. | 204/159.14 |
| 4,047,531 | 9/1977 | Karami | 128/287 |
| 4,226,237 | 10/1980 | Levesque | 128/287 |

Primary Examiner—Robert W. Michell
Assistant Examiner—T. J. Wallen
Attorney, Agent, or Firm—Jason Lipow

[57] ABSTRACT

Peat moss having increased wettability and increased brightness while maintaining its absorbency and structural integrity is provided. The peat moss is treated so as to chemically graft onto its structure, unhydrolized polymeric chains of the general formula:

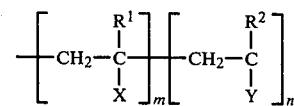

wherein $R^1$ and $R^2$ are selected from the group consisting of hydrogen and $-CH_3$, X and Y are selected from the group consisting of $-CN$, $-COONH_2$ and $-OCH_3$ and wherein m and n are integers which when summed together equal at least 500.

20 Claims, No Drawings

BRIGHT PEAT MOSS PRODUCT AND METHOD FOR MAKING SAME

TECHNICAL FIELD

The present invention relates to a process for producing a bright peat moss product that is still capable of being used as an absorbent.

BACKGROUND OF THE ART

Peat moss belongs to the genus sphagnum and is a plant that grows from the top while the bottom part dies and changes into peat. Chemically, peat moss consists of about 50%, by weight, lignin and humic acid with the remainder consisting of hemicellulose, cellulose, waxes and nitrogen compounds. Physically, peat moss leaf is one cell layer thick, the cells having thin, lignified walls. The cells or pores of the leaflike structure are generally evenly distributed about the surface of the leaf and range in size from about 15 to 40 microns in diameter. It is on the surface and on the walls of the pores that the lignin is primarily distributed and as a result, the peat exhibits a dark brown to yellow color.

Primarily because of the pore structure, peat moss has the ability to absorb and hold relatively large amounts of water within the capillaries formed by the pores, and so has found considerable use in the horticultural industry. Additionally, peat moss has been used in water treatment techniques.

It has also been suggested by various prior investigators that peat moss be used as an absorbent dressing for body fluids in such products as sanitary napkins, tampons, or diapers. Such use, however, has not found wide acceptance and it is believed that this lack of acceptance is related to the problem of color, i.e., the consumer or user does not like the unduly dark color of peat moss.

While many processes exist for bleaching lignin, particularly lignin found in wood pulp, it is believed that no such prior process could produce a peat moss product which has the satisfactorily high brightness to suit consumer preferences. One achievement in this direction is described in a commonly assigned patent application filed in the U.S. Pat. and Trademark Office in Feb. 21, 1978 as Ser. No. 879,833, now U.S. Pat. No. 4,170,515 by Drs. Jean-Marc Lalancette and Bernard Coupal. In accordance with that application, peat moss may be bleached, using a bleaching process which takes place under acid conditions, to obtain structurally integral product having a color level on the Hunter Scale of up to about 75. Unfortunately, when attempts are made to increase the severity of the bleaching process or prolong the process in an effort to obtain still whiter peat moss, the structural integrity of the product is destroyed, the leaf collapses and the structure creating the capillaries responsible for the absorptive properties of the peat moss disappears. The reason for this is believed to be that the same lignin and humic acid, disposed on the surface of the leaf, which gives peat moss its dark color also prevents the peat moss from collapsing and is responsible for the property of maintaining capillary structure when wet. To bleach peat moss brighter in color than about 75 on the Hunter Scale requires removal of the lignin which, in turn, causes the undesirable collapse of the peat moss structure. Accordingly, bright absorbent peat moss and a method for making the same has heretofore eluded the art.

SUMMARY OF THE INVENTION

It has now been discovered that peat moss may be provided by a process wherein the peat moss is substantially brightened without destroying its structural integrity. More specifically, a process has been devised for modifying the surface of the peat moss so that the undesirable color effect of the lignin is mitigated without removal of the lignim, thereby preserving the native structure of the peat moss. Not only is the native structure of the product preserved but it has also been discovered that the resulting product has increased wettability and at least comparable absorbency as compared to the untreated product.

In accordance with this invention, peat moss is treated so as to chemically graft onto its structure unhydrolyzed polymeric chains of the general formula:

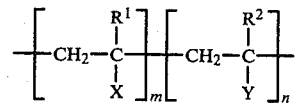

wherein $R^1$ and $R^2$ are selected from the group consisting of hydrogen and $-CH_3$, X and Y are selected from the group consisting of $-CN$, $-COONH_2$ and $-OCH_3$ and wherein m and n are integers which when summed together equal at least 500. Preferably, the polymer chains are formed from monomers selected from the group consisting of acrylonitrile, acrylic acid, acrylamide and derivatives and mixtures thereof.

It has been discovered that by undergoing this grafting treatment, the grafted peat moss can exhibit increases in brightness to values of more than 80 and preferably more than 85 units when measured on the Hunter C Scale (ASTM Test D2244) and that this is true even when starting with peat moss which has already undergone a brightening process such as, for example, the aforementioned bleaching process described in the above identified patent application Ser. No. 879,833 now U.S. Pat. No. 4,170,515. Additionally, it has been discovered that this occurs without detrimental effects on absorbency or wettability. In fact, it has been found that wettability, as measured by the Drop Test described herein, will be substantially increased. Surprisingly, for reasons not yet understood, it has been discovered that if the grafting process used for peat moss includes a hydrolysis step such as has been employed in prior processes such as that described in U.S. Pat. No. 3,889,678, issued on June 17, 1975 to P. K. Chatterjee and R. F. Schwenker, Jr., then the advantageous brightening effect is totally lost and the resulting product has a permanent yellowish cast.

DESCRIPTION OF THE PREFERRED EMBODIMENTS

The starting peat moss is preferably that portion of a peat bog obtained from the top 30 cm depth and is of the Sphagnum type. While it is of course preferable to start with the most absorbent peat moss if the ultimate use is for absorbent products, this is not essential to the working of this invention. However, preferably the peat moss should be selected to have the capacity of holdingg at least 15 times its weight of water.

The raw peat moss is screened to remove roots and branches. It has been found that the portion of the untreated peat moss which passes through a ten mesh screen and remains on a 100 mesh screen is the most absorbent. Accordingly, the preferred starting peat moss is screened to be from about 0.15 mm (100 mesh) to about 1.8 mm. (10 mesh) in size.

The starting native peat moss has a whiteness of about 50 to about 55 as measured on the Hunter Scale. It is therefore preferable to treat this starting material by bleaching the same prior to applying the teachings of this invention so that the highest degree of whiteness can be obtained. A suitable bleaching system now known in the art is described in the above-identified U.S. Pat. application Ser. No. 879,833 now U.S. Pat. No. 4,170,515. In accordance with this process, screened peat moss is formed into a slurry of a pumpable consistency and then treated with active chlorine in combination with an alkali metal or alkaline earth metal carbonate or hydroxide. The treatment is carried out at a pH of 7 or less. Preferably the treatment consists of treating the peat moss with calcium or sodium carbonate or hydroxide while maintaining the pH at 7 followed by adding gaseous chlorine to the slurry along with sodium or calcium hypochlorite, again while maintaining the slurry at pH 7 or less. This treatment is followed by dewatering the slurry and then washing with acid to produce a bleached peat moss which has a whiteness value of up to about 75 on the Hunter Scale.

A preferable method of bleaching is to employ multiple steps in a bleaching sequence that includes first, chlorination using gaseous chlorine, then caustic extraction and finally, hypochlorite bleaching. By this method, peat moss having a whiteness of as high as 80 on the Hunter Scale may be obtained.

Irrespective of how the starting peat moss is bleached, in accordance with this instant invention, the bleached peat moss is slurried in water and then washed in acid to remove undesirable cations such as calcium or sodium. The washed peat moss is then again slurried in water and monomer. In each case, the peat moss should be slurried in the minimum quantity of monomer required to insure a uniform dispersion and reaction. Generally, a slurry of preferably about 2%, by weight of solids ensures a good dispersion of the peat moss and an economical and efficient use of chemicals.

The monomers added to the slurry from which the polymer chains are formed and grafted to the peat are all vinyl compounds having the general structure

wherein R is selected from the group consisting of —H, or —CH$_3$ and Z is selected from the group consisting of —CN, —COOH, —COONH$_2$, or —OCH$_3$. Mixtures of these monomers may also be employed. Preferred monomers are those selected from the group consisting of acrylonitrile, acrylic acid, acrylamide or such derivatives of acrylonitrile such as ethyl acrylate, methyl methacrylate or mixtures of these such as acrylonitrile-ethyl acrylate or acrylonitrile-methyl methacrylate.

While the detailed mechanism of polymerizing and grafting these monomers onto the peat moss is not fully known, it is believed that one possibility is that grafting and polymerization takes place through a free radical mechanism whereby the free radical is situated on the lignin covered peat moss surface which surface serves as a reducing agent and the polymeric chain attaches to this reducing agent through a carbon linkage to produce a grafted product.

The grafting reaction may be initiated with an ionic initiator (e.g., alkali hydroxides), a cationic initiator (e.g., a Lewis acid such as boron trifluoride), or even radiation (e.g., ultraviolet, gamma, or X-radiation). It is preferred, however, that the polymerization and grafting be carried out by the free-radical copolymerization mechanism using a free radical initiator such as, for example, ceric ion, ferrous ion, cobaltic ion, cuprous ion, and the like. The ceric ion initiator is preferred.

Because most free radical reactions are inhibited by the presence of oxygen, it is desirable to flush out essentially all the oxygen from the reaction mixture and reaction vessels by bubbling a non-oxidizing gas such as nitrogen, helium, argon, etc. through the system prior to the addition of the free radical initiator. It is also been found advantageous to add the free radical initiator after the monomers have been dispersed in the peat moss-water slurry.

The pH range used for the reaction depends on the particular initiator used. One could employ anywhere from a highly acidic pH to a highly basic pH, depending on the particular initiator. For the preferred ceric ion initiator, the pH should be acid, i.e., less than seven, and preferably should be about 1 to about 3.

The temperature of the reaction may be anywhere from room temperature (about 20–30° C.) to the normal boiling point of the lowest boiling component of the reactive mixture. At elevated pressures, higher temperatures may be employed. The reaction mixture may also be cooled below room temperature if desired.

The resulting product is a peat moss having the above-defined unhydrolyzed polymer chains grafted thereto, said grafted chains being present in a quantity of about 5 to about 100% of the weight of the original peat moss (on a bone dry peat moss basis). Brightness of the resulting product is increased to a value of more than 80 and preferably more than 85 units on the Hunter Scale.

The wettability of the resulting product is substantially increased as measured by the Drop Test. The Drop Test represents the required time in seconds for a single drop of a 1%, by weight, sodium chloride water solution to be completely absorbed and disappear when dropped onto the flat and dry surface of a peat moss web. In the case of the peat moss of this invention, the wettability increased such that a drop disappears in less than one second. In fact the disappearance time is essentially instantaneous.

Absorbency also increases slightly as measured by the following test:

About 1 gram of the peat moss of this invention is dried at 105° C. for one hour and is than immersed in a 1% by weight sodium chloride water solution for 5 minutes to assure complete saturation of the peat moss. Wet peat moss is then collected by filtering from the excess sodium chloride solution and is than weighted. The absorbency is expressed as the ratio of the wet weight of the peat moss to its dry weight. The product of this invention will exhibit an absorbency (weight ratio) of at least 10 and preferably at least 15 grams wet per gram dry.

In commonly assigned U.S. Pat. Nos. 3,889,678 and 4,105,033, the grafting of hydrolyzed polymer chains onto wood pulp and starch are described as increasing the absorbency of these materials. It has been discovered that if these teachings are followed in the case of grafting to peat moss, the main object of this invention, namely, the increase in brightness is frustrated. While a highly absorbent product results, the effect of hydrolysis of grafted peat is disadvantageously to produce a yellow-like product having permanently reduced whiteness.

Having described embodiments of the process and product of the present invention, the following examples describe specific preferred embodiments. The illustrated experimental conditions are not intended to limit the scope of the present invention. As used in these examples, all percentages are by weight of aqueous slurry.

EXAMPLE I

One gram samples of peat moss, having been screened to pass through a 10 mesh screen and remain on a 100 mesh screen are bleached to the brightness level of 80 on the Hunter Scale by the multistage bleaching process of chlorination, caustic extraction and hypochlorite treatment. The samples are each dispersed in a mixture of 25 ml of water and 15 ml of N hydrochloric acid for five minutes. The peat moss is then collected by filtration and transferred to 125 ml stoppered flasks. Various quantities of acrylonitrile monomer is added to each flask with an appropriate amount of nitric acid and water. The peat moss slurry is stirred for a few minutes to ensure good dispersion, and then various quantities of ceric ammonium nitrate in a nitric acid solution is added with continuous stirring for a few minutes.

It is observed that the peat moss volume increases significantly in the first ten minutes of the reactions. The grafting is terminted after an hour, and the grafted peat is filtered, washed with water and dried. The percent add-on, based on bone dry peat moss, is calculated.

It is found that the grafting only occurs in highly acidic conditions, and there is no grafting in neutral or basic slurries. It is also found that the percent of add-on increases with ceric ion concentration and with concentration of acrylonitrile. The following Table I summarizes the data obtained:

TABLE I

Effect of Ceric Concentration and Acrylonitrile Concentration on the Grafting of Acrylonitrile onto Peat Moss

| Sample | Ceric Ion (mmole/l) (at 1.72% peat moss, 6.4% acrylonitrile) | % Add-On |
| --- | --- | --- |
| 1 | 4 | 10.7 |
| 2 | 6 | 34.7 |
| 3 | 8 | 52.6 |
| 4 | 12 | 146.3 |
| 5 | 16 | 263.9 |

| Sample | Acrylonitrile (%) (at 1.72% peat, 10 mmole/l) | % Add-On |
| --- | --- | --- |
| 6 | 1.6 | 7.6 |
| 7 | 3.2 | 16.8 |
| 8 | 6.4 | 75.1 |
| 9 | 12.8 | 96.7 |
| 10 | 16.0 | 80.0 |

The grafted polyacrylonitrile peat exhibits an exceptional bulkiness, an enhanced wettability (to the point of instantaneous absorption, i.e., 0 second by drop test) and a surprising brightness and color stability and can absorb more than 18 times its own weight of 1% sodium chloride solution.

EXAMPLE II

Samples of one gram of peat moss, previously bleached by the chlorination, caustic extraction and hypochlorite sequence to a brightness level of 80 on the Hunter Scale, are dispersed in a mixture of 25 ml of water and 15 ml of hydrochloric acid normal for five minutes before being grafted with acrylic acid. The grafting is carried out in 125 ml stoppered flasks. Various amounts of water are first added to each flask and then various quantities of acrylic acid are introduced. The flasks are stoppered and shaken for a few minutes before the addition of ceric ammonium nitrate. After half an hour, the peat moss is collected and washed with water.

It is found that grafted polyacrylic acid peat moss exhibits an instantaneous wettability even at very low percent add-ons. The peat moss bulkiness increases with the degree of grafting, and the percent add-on can be higher than 90% under nitrogen conditions. Grafted peat moss also shows a substantial gain in brightness and an absorption capacity as high as 21 times its own weight of aqueous solution.

The following Table II summarizes some of the experimental conditions of the grafting of acrylic acid onto peat:

TABLE II

Grafting of Acrylic Acid onto Peat (Peat 1.8%, Acrylic Acid 8%)

| Sample | Ceric (mmole/l) | % Add-On |
| --- | --- | --- |
| 1 | 4 | 1.62 |
| 2 | 6 | 7.08 |
| 3 | 8 | 8.50 |
| 4 | 10 | 14.95 |
| 5 | 12 | 31.75 |
| 6 | 10(Nitrogen Condition) | 90.00 |

EXAMPLE III

A four gram sample of peat moss, bleached by the chlorination, caustic extraction and hypochlorite sequence, is first washed with 150 ml of 0.3 N hydrochloric acid and grafted with acrylamide. This is accomplished by placing the peat moss in a 500 ml flask with 100 ml of water and 10 g of the acrylamide and stirring the slurry for 5 minutes. 125 ml of ceric ammonium nitrate solution of 20 mmole per liter in nitric acid normal is added, and the reaction is carried out for two hours under nitrogen conditions. At the end of the reaction, the resulting grafted peat moss is filtered and washed with water. The grafted acrylamide peat moss is exceptionally bright and hydrophylic. The peat moss is highly bulky possesses an absorbency of above 25 times its own weight of 1% sodium chloride solution, and can be wetted instantaneously.

I claim:

1. Bright, absorbent, highly wettable peat moss having grafted thereon unhydrolyzed polymeric chains of the general formula:

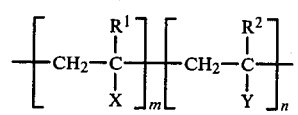

wherein $R^1$ and $R^2$ are selected from the group consisting of hydrogen and —$CH_3$, X and Y are selected from the group consisting of —CN, —COOH, —COONH$_2$, and —OCH$_3$; wherein m and n are integers which when summed together equal at least 500;

said grafted peat having a brightness of more than 80 on the Hunter Scale while still maintaining its capillary structure.

2. The grafted peat moss of chain 1 wherein said polymeric chains are formed from monomers selected from the group consisting of acrylonitrile, acrylic acid, acrylamide and derivatives and mixtures thereof.

3. The grafted peat moss of claim 2 where said polymeric chains are formed from acrylic acid.

4. The grafted peat moss of claim 2 wherein said polymeric claims are formed from acrylonitrile.

5. The grafted peat moss of claim 1 wherein said polymeric chains are present in a quantity of about 5 to about 100% by weight of the original peat moss, on a bone dry basis.

6. The grafted peat moss of claim 1 having a brightness of more than 85 on the Hunter scale.

7. The grafted peat moss of claim 1 having a Drop test value of less than 1 sec.

8. The grafted peat moss of claim 1 having an absorbency ratio of at least 10 grams wet per gram dry.

9. The grafted peat moss of claim 1 having an absorbency ratio of at least 15 grams wet per gram dry.

10. A method of producing bright, absorbent, highly wettable peat moss comprising:

grafting to peat moss unhydrolyzed polymeric chains of the general formula:

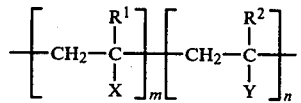

wherein R$^1$ and R$^2$ are selected from the group consisting of hydrogen and —CH$_3$, X and Y are selected from the group consisting of —CN, —COOH, —COONH$_2$, and —OCH$_3$; wherein m and n are integers which when summed together equal at least 500, whereby said grafted peat moss has a brightness of more than 80 on the Hunter Scale.

11. The method of claim 10 wherein said polymeric chains are formed by reacting said peat moss with monomers selected from the group consisting of acrylonitrile, acrylic acid, acrylamide and derivatives and mixtures thereof.

12. The method of claim 11 wherein said monomer is acrylic acid.

13. The method of claim 11 wherein said monomer is acrylamide.

14. The method of claim 10 wherein said grafting is carried out by reacting of said monomers with peat moss in the presence of an ionic initiator.

15. The method of claim 11 wherein said peat moss is first bleached to a brightness up to about 75 on the Hunter Scale.

16. The method of claim 11 wherein said peat moss is first screened to remove roots and branches and further screens to pass through a 10 mesh screen and assumption on a 100 mesh screen.

17. A product for absorbing body fluid comprising as an absorbent element thereof:

bright, absorbent, highly wettable peat moss having grafted thereon unhydrolyzed polymeric chains of the general formula:

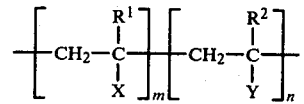

wherein R$^1$ and R$^2$ are selected from the group consisting of hydrogen and —CH$_3$, X and Y are selected from the group consisting of —CN, —COOH, —COONH$_2$, and —OCH$_3$; wherein m and n are integers which when summed together equal at least 500;

said grafted peat having a brightness of more than 80 on the Hunter Scale.

18. The product of claim 17 as a disposable diaper.
19. The product of claim 18 as a sanitary napkin.
20. The product of claim 18 as a catamenial tampon.

* * * * *